United States Patent [19]

Shetty et al.

[11] Patent Number: 4,639,529
[45] Date of Patent: Jan. 27, 1987

[54] ANALGESIC AND ANTI-INFLAMMATORY COMPOUNDS

[75] Inventors: Bola V. Shetty, Stamford, Conn.; Arthur McFadden, East Brunswick, N.J.; Peter Hofer, Liestel, Switzerland

[73] Assignee: The Purdue Frederick Company, Norwalk, Conn.

[21] Appl. No.: 621,680

[22] Filed: Jun. 18, 1984

Related U.S. Application Data

[60] Division of Ser. No. 349,992, Feb. 19, 1982, Pat. No. 4,476,311, which is a continuation of Ser. No. 129,578, Dec. 3, 1980, abandoned.

[51] Int. Cl.$^4$ .......................................... C07D 207/12
[52] U.S. Cl. .................................................. 548/550
[58] Field of Search ................ 548/530, 531, 550, 551

[56] References Cited

U.S. PATENT DOCUMENTS 4,476,311 10/1984 Shetty et al. ........................ 548/531

FOREIGN PATENT DOCUMENTS

| 2097038 | 4/1972 | France . | |
|---|---|---|---|
| 56-59751 | 5/1981 | Japan | 548/551 |
| 56-59752 | 5/1981 | Japan | 548/551 |
| 56-59753 | 5/1981 | Japan | 548/551 |
| 56-59754 | 5/1981 | Japan | 548/551 |

OTHER PUBLICATIONS

Buzas et al., "Synthesis and Pharmacological Properties of New Derivatives of 2-Pyrrolidone-4-Carboxylic Acids", Chemical Abstracts 78: 43180m.
Pessun et al., "1-(1-Aryl-2oxo-Piperazinocarbonyl)-Pyrrolidines, Chemical Abstracts 77: 126688p.
Castagnoli, Jr.; J. Org. Chem.; 34, 1969, pp. 3187-3189.

*Primary Examiner*—Joseph Paul Brust
*Attorney, Agent, or Firm*—Steinberg & Raskin

[57] ABSTRACT

Analgesic and anti-inflammatory compounds are provided. These compounds possess the following general formula:

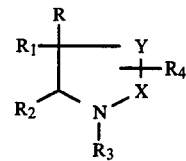

wherein
R = —COOR$_5$, —CH$_2$CO$_2$H,

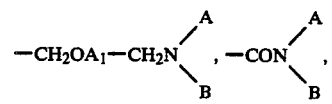

wherein
A and B = hydrogen, lower alkyl, hydroxy alkyl, lower alkyl amine, substituted lower alkyl amine, aminoalkyl, substituted aminoalkyl;
R$_5$ = lower alkyl;
R$_1$ = aryl, substituted aryl, aralkyl, alkyl, hydrogen, substituted aralkyl and heterocycle;
R$_2$ = aryl, substituted aryl, aralkyl, alkyl, substituted aralkyl, heterocycle, substituted heterocycle, biphenyl, substituted biphenyl, naphthyl, and substituted naphthyl;
R$_3$ = aryl, substituted aryl, hydrogen, aralkyl, substituted aralkyl, alkyl, heterocycle and substituted heterocycle;
R$_2$ and R$_3$ together form a ring;
R$_4$ = hydrogen, phenyl, substituted phenyl, heterocycle; alkyl, substituted alkyl; or, R$_1$ and R$_4$ may form a ring;

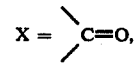

—CH$_2$—;
Y = —S—CHR$_4$—, —O—OHR$_4$—, —CHR$_4$—, —CR$_6$-R$_7$—CHR$_4$,

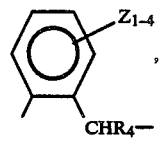

wherein
R$_6$ = same as R$_4$;
R$_7$ = same as R$_4$; R$_6$ and R$_7$ may form a ring; and
Z = hydrogen, halogen, alkyl, substituted alkyl, hydroxy, alkyloxy, amino, substituted amino, nitro, aryl, substituted aryl, aryloxy.

3 Claims, No Drawings

ANALGESIC AND ANTI-INFLAMMATORY COMPOUNDS

This is a division of application Ser. No. 349,992, filed 2/19/82, now U.S. Pat. No. 4,476,311, issued 10/9/84, which is a continuation of Ser. No. 129,578, filed 12/3/80, now abandoned.

BACKGROUND OF THE INVENTION

There is, and has been for many years, a continuous search for new analgesic and anti-inflammatory agents.

Unfortunately, it is impossible to predict by structure of the compound whether a compound will be effective as an analgesic and/or an anti-inflammatory agent. Still further, as to those compounds which are found to be effective as analgesics and/or anti-inflammatory agents, the degree of effectiveness and the degree, or lack of degree of side effects is of considerable importance and is totally unpredictable.

SUMMARY OF THE INVENTION

It is accordingly a primary object of the present invention to provide new analgesic, anti-inflammatory and CNS active agents.

It is another object of the present invention to provide a new series of compounds which possess effective analgesic anti-inflammatory and CNS action.

It is yet a further object of the present invention to provide for the production of these new compounds.

Other objects and advantages of the present invention will be apparent from a further reading of the specification and of the appended claims.

With the above and other objects in view, the present invention mainly comprises compounds of the formula:

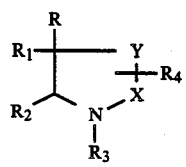

wherein
R=—COOR$_5$, —CH$_2$CO$_2$H,

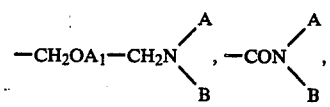

wherein
A and B=hydrogen, lower alkyl, hydroxy alkyl, lower alkyl amine, substituted lower alkyl amine, aminoalkyl, substituted aminoalkyl; R$_5$=lower alkyl;
R$_1$=aryl, substituted aryl, aralkyl, alkyl, hydrogen, substituted aralykl and heterocycle;
R$_2$=aryl, substituted aryl, aralkyl, alkyl, substituted aralkyl, heterocycle, substituted heterocycle, biphenyl, substituted biphenyl, naphthyl, and substituted anphthyl; or R$_2$ and R$_3$ together may form a ring
R$_3$=aryl, substituted aryl, hydrogen, aralkyl, substituted aralkyl, alkyl, heterocycle and substituted heterocycle;
R$_4$=hydrogen, phenyl, substituted phenyl and heterocycle; alkyl, substituted alkyl; or R$_1$ and R$_4$ may form a ring
X=C=O and —CH$_2$—;
Y=—S—CHR$_4$—, —O—CHR$_4$—CHR$_4$—CR$_6$-R$_7$—CHR$_4$—,

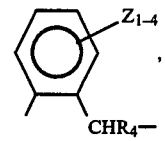

wherein
R$_6$=same as R$_4$
R$_7$=same as R$_4$, R$_6$ and R$_7$ may form a ring, and
Z=hydrogen, halogen, alkyl, substituted alkyl, hydroxy, alkyloxy, amino, substituted amino, nitro, aryl, substituted aryl, aryloxy.

In connection with the substituents R$_1$, R$_2$ and R$_3$, the preferred aryl group is phenyl. The preferred substituted aryl are the phenyl substituted by lower alkyl, hydroxy, carboxylic, lower alkoxy, and halogen. The preferred heterocyclic radicals for R$_1$, R$_2$, R$_3$ and R$_4$ are 5 and 6 member rings with nitrogen and/or oxygen, such as pyrrolidine, pyrimidine and the like.

DESCRIPTION OF PREFERRED EMBODIMENTS

The following examples are given to further illustrate the present invention. The scope of the invention is not, however, meant to be limited to the specific details of the examples: in most cases one isomer (probably cis) could be isolated by direct crystallization:

EXAMPLE 1

Preparation of 1-Benzyl-4-N,N-Dimethylaminomethyl-5-(3-Methoxyphenyl)Pyrrolidin-2-One Hydrochloride

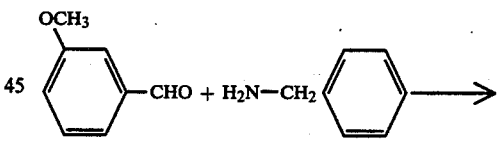

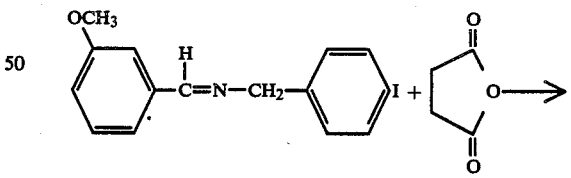

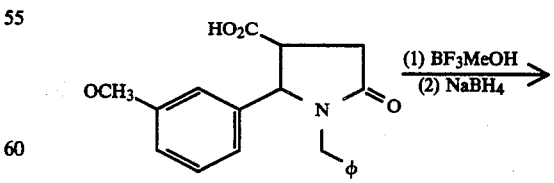

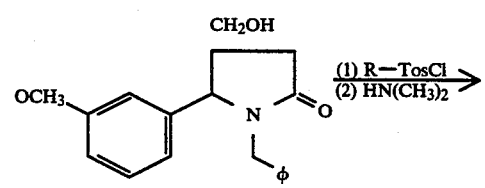

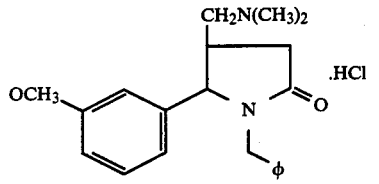

(A) 3-Methoxybenzylidenebenzylamine

A solution of 100 gm. of 3-methoxybenzaldehyde. 78.7 gm. of benzylamine, and 800 ml. of anhydrous ether was refluxed for 14 hours and then concentrated in vacuo to an oil. Distillation provided 144.3 gm. of clear oil, b.p. 152°-154° (1.2 Torr).

(B) 1-Benzyl-2-(3-methoxyphenyl)-5-oxopyrrolidin-3-carboxylic acid

To 450 ml. of xylene was added 143.3 gm of 3-methoxyphenylbenzylidenebenzylamine and 63.9 gm. of succinic anhydride. The solution was refluxed for 15 hours, cooled and extracted with saturated sodium bicarbonate solution. After washing the basic solution with ether, the aqueous phase was acidified with concentrated hydrochloric acid to provide a white gum. The gum was dissolved in ether, dried ($Na_2SO_4$), filtered and concentrated in vacuo to a semi-solid which was titurated with anhydrous ethyl ether and the resultant solid removed by filtration and discarded. Concentration in vacuo provided 18.5 g of the desired product as a gum.

(C) Methyl 1-Benzyl-2-(3-methoxyphenyl)-5-oxopyrrolidin-2-carboxylate

A solution of 1-benzyl-2-(3methoxyphenyl)-5-oxopyrrolidin-3-carboxylic acid in 647 ml. of 10-15% boron fluoride-methanol was refluxed for 4 hours. Concentration in vacuo provided an orange oil which was dissolved in chloroform, washed with a saturated sodium bicarbonate solution, and dried ($Na_2SO_4$). Filtration and concentration in vacuo provided 42.1 gm. of the product as an orange oil.

(D) 1-Benzyl-4-hydroxymethyl-5-(3-methoxyphenyl)pyrrolidin-2-one

To 42.1 gm. of methyl 1-benzyl-2-(3-methoxyphenyl)-5-oxopyrrolidin-3-carboxylate in 436 ml. of absolute methanol was slowly added at −10° to −5°, 37.9 gm. of sodium borohydride. The reaction mixture was left in the ice bath until it came to ambient temperature. Concentration in vacuo provided a white gum which was suspended in water and heated to 50° C. The gum was extracted with chloroform, dried ($Na_2SO_4$), filtered, and concentrated in vacuo to yield 22.8 gm. of yellow oil.

(E) 1-Benzyl-4-(p-toluenesulfonyloxymethyl)-5-(3-methoxyphenyl)pyrrolidin-2-one To 21.4 gm. of 1-benzyl-4-hydroxymethyl-5-(3methoxyphenyl)pyrrolidin-2-one in 40 ml. of potassium dried pyridine was slowly added at −4° to −7°, 14.4 gm of p-toluenesulfonyl chloride. The reaction mixture was stirred for 3 hours at 15° and then diluted with 180 ml. of 10% hydrochloric acid. The gum was extracted with chloroform, dried ($Na_2SO_4$), filtered and concentrated in vacuo to provide 24.6 gm. of the desired product as an oil. ir ($CHCl_3$): 1165-1195 $cm^{-1}$; 1335-1375 $cm^{-1}$

(F) 1-Benzyl-4-N,N-dimethylaminomethyl-5-(3-methoxyphenyl)pyrrolidin-2-one hydrochloride A solution of 3.0 gm. of 1-benzyl-4-(p-toluenesulfonyloxymethyl)-5-(3-methoxyphenyl)pyrrolidin-2-one, 60 ml. of dimethylformamide, and 6.0 gm. of 40% aqueous dimetylamine was refluxed for 4 hours. The reaction was poured into 300 ml. of ice and set overnight. The aqueous solution was acidified with 10% hydrochloric acid and extracted with ether; basification of the acid phase with potassium carbonate followed by extraction with ether which was then dried ($Na_2SO_4$), filtered and concentration in vacuo gave yellow oil. After dissolving the oil in anhydrous ether, dry hydrogen chloride gas was bubbled in to form the hydrochloride. The solid was collected by filtration and washed twice with anhydrous ether. Recrystallization from acetonitrile provided 0.8 gm. of colorless crystals, mp 207°-210°.

Analysis: Calculated for $C_{21}H_{27}ClN_2O_2$ C, 67.27; H, 7.26; Cl, 9.46; N, 7.47. Found: C, 67.03; H, 7.47; Cl, 9.68; N, 7.47.

EXAMPLE 2

Preparation of 4-Dimethylaminomethyl-5-(3-Methoxyphenyl)-1-Phenylpyrrolidin-2-One

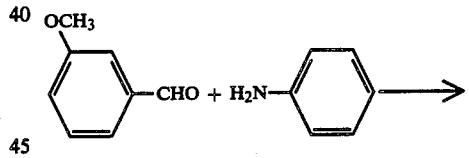

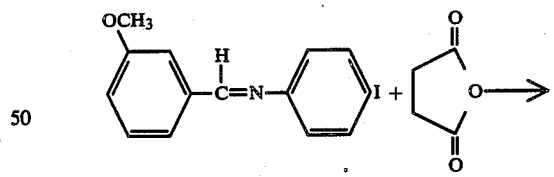

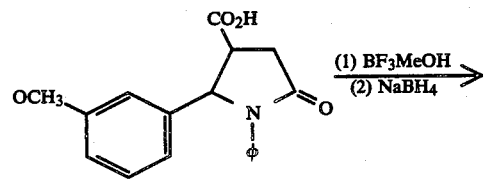

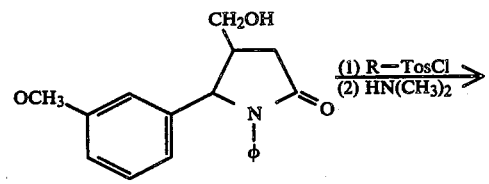

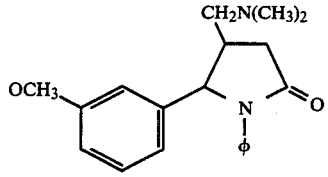

(A) 3-Methoxybenzylidenaniline

A solution of 85.4 gm. of 3-methoxybenzaldhyde, 58.7 gm. of aniline, and 185 gm. of 3 A molecular sieves in 700 ml. of anhydrous ether was refluxed for 16 hours. The ether was dried ($Na_2SO_4$), filtered, and concentrated in vacuo to an oil which upon distillation provided 93.2 gm of oil. b.p. 141°–143°/0.5 Torr.

(B) 2-(3-Methoxyphenyl)-5-oxo-1-phenylpyrrolidin-3-carboxylic acid

A solution of 42.3 gm. of 3-methoxybenzylidenaniline, 20 gm. of succinic anhydride and 200 ml. of xylene was refluxed for 16 hours. The crude product was obtained as a solid via the same workup used for example 1B. Recrystallization from ethyl acetate followed by a second recrystallization from acetonitrile provided 21.0 gm. of colorless crystals, m.p. 145°–149°.

Analysis: Calculated for $C_{18}H_{17}NO_4$ C, 69.44%; H, 5.51%; N, 4.50%. Found: C, 69.11%; H, 5.41%; N, 4.35%.

(C) Methyl-2-(3-Methoxyphenyl)-5-oxo-1-phenylpyrrolidin-3-carboxylate

A solution of 25.0 gm. of 2-(3-methoxyphenyl)-5-oxo-1-phenylpyrrolidin-3-carboxylic acid in 200 ml 10–15% boron fluoride-methanol was refluxed for 8 hours and upon following the workup for example 1C the product was obtained as an oil.

(D) 4-Hydroxymethyl-5-(3-methoxyphenyl)-1-phenylpyrrolidin-2-one

To 26.7 gm. of methyl 2-(3-methoxyphenyl)-5-oxo-1-phenylpyrrolidin-3-carboxylate in 200 ml of absolute methanol was added slowly at 0°–10° 24.8 gm. of sodium borohydride. The reaction was run and worked up following the procedure of example 1D. Drying ($Na_2SO_4$), filtration, and concentration in vacuo provided 17.2 gm. of colorless crystals, m.p. 123°–126°.

(E) 5-(3-Methoxyphenyl)-1-phenyl-4-(p-toluenesulfonyloxymethyl)pyrrolidin-2-one To 17.2 gm. of 4-hydroxymethyl-5-(3-methoxyphenyl)-1-phenylpyrrolidin-2-one in 35 ml. of dry pyridine was added at 5°–10° 12.2 gm of p toluenesulfonyl chloride over one hour. Workup of the reaction following the procedure given in example 1E provided 17.6 gm of product as a crude oil.

(F) 4-Dimethylaminomethyl-5-(3-methoxyphenyl)-1-phenylpyrrolidin-2-one

To 22.0 gm. of 5-(3-methoxyphenyl)-1-phenyl-4-(p-toluenesulfonyloxymethyl)pyrrolidin-2-one in 150 ml. of dimethylformamide was added 21 ml. of 40% aqueous dimethylamine, the solution refluxed for 3 hours and then 21 ml. more of 40% aqueous dimethylamine added and reflux continued for an additional 3 hours. After cooling the reaction was decanted into ice water and acidified. Extraction with ether followed by basification of the aqueous phase with potassium carbonate yielded a semi-solid which was extracted with chloroform, dried ($Na_2SO_4$), filtered and concentrated in vacuo to a solid. Recrystallization from acetonitrile provided 7.0 gm. of beige crystals, m.p. 88°–92°.

Analysis: Calculated for $C_{20}H_{24}N_2O_2$ C, 74.04%; H, 7.46%; N, 8.64%. Found: C, 74.71%; H, 7.32%; N, 8.43%.

EXAMPLE 3

Preparation of 1-Benzyl-4-N,N-Dimethylaminomethyl-5-(3-Hydroxyphenyl)Pyrrolidin-2-One Hemihydrate

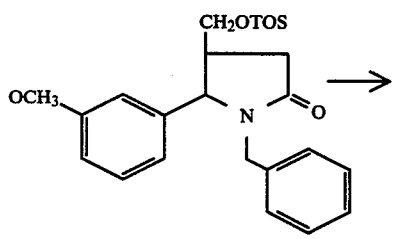

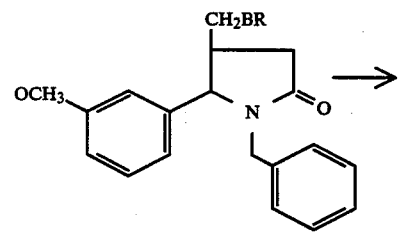

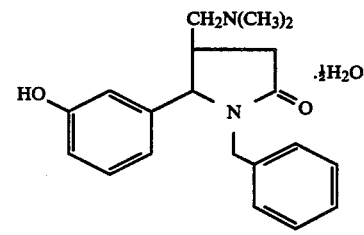

(A) 1-Benzyl-4-bromomethyl-5-(3-hydroxyphenyl)pyrrolidin-2-one

A mixture of 40.5 gm. of 1-N-benzyl-5-(3-methoxyphenyl-4-(p-toluenesulfonyloxymethyl)pyrrolidin-2-one, 160 ml. of acetic acid, and 100 ml. of 48% hydrobromic acid was added and refluxed for 6 hours; an additional 100 ml. of 48% hydrobromic acid was added and reflux continued for an additional 3 hours. The reaction mixture was cooled and poured into 2.0 l. of ice water; the resulting gum was extracted with chloroform, washed with a saturated sodium bicarbonate solution, dried ($Na_2SO_4$), filtered and concentrated in vacuo to 24.3 g. of a semi-solid.

(B)
1-Benzyl-4-N,N-dimethylaminomethyl-5-(3-hydroxyphenyl)pyrrolidin-2-one hemihydrate A solution of 24.3 gm. of 1-N-benzyl-4-bromomethyl-5-(3-hydroxyphenyl)pyrrolidin-2-one, 300 ml. of dimethylformamide, and 0.10 gm. of sodium bromide was brought to reflux and N,N-dimethylamine gas was bubbled into the reaction during the 6 hour reflux period. Upon cooling, the reaction mixture was poured into 1.0 l. of water and extracted with a 2:1 mixture of ether-chloroform. The aqueous layer was basified with a saturated sodium bicarbonate solution and extracted with a 1:1 ether-chloroform solution. Drying (Na$_2$SO$_4$), filtration, and concentration in vacuo provided an oil. Trituration of the oil with acetonitrile gave a light tan product which was then dissolved in a minimal amount of dilute hydrochloric acid and filtered. Basification with potassium carbonate provided a gum which was extracted with chloroform, dried (Na$_2$SO$_4$), filtered, and concentrated in vacuo to a brittle oil which upon trituration with a small amount of acetonitrile provided 1.68 g of colorless crystals, m.p. 159°–160° C.

Analysis: Calculated for C$_{20}$H$_{24}$N$_2$O$_2$·½H$_2$O C, 72.08%; H, 7.50%; N, 8.40%. Found: C, 72.29%; H, 7.23%; N, 8.16%.

EXAMPLE 4

Preparation of 2,3-Diphenyl-3-Hydroxymethyl-1-Methyl Piperidine

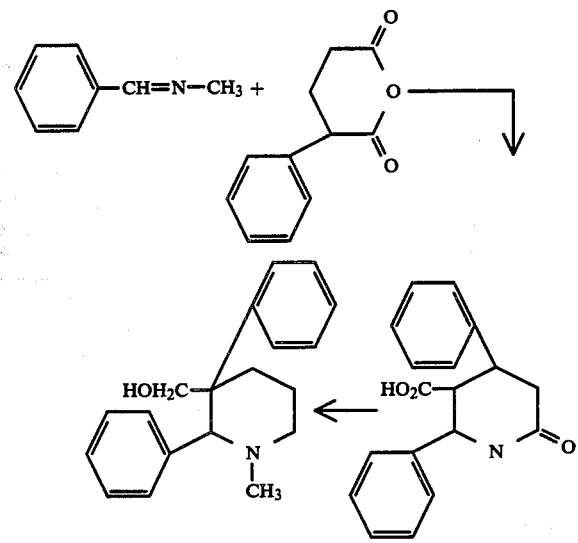

8.3 g (0.0436 mole) of 2-phenylglutaric anhydride and 5.2 g (0.0436 mole) of Schiff base, provided from benzaldehyde and methylamine, are refluxed at 140° in 50 ml of xylene for 12 hr. After cooling the solid is collected and washed with xylene and ether: 7.6 g of 2,3-diphenyl-1-methyl-piperdin-6-one-3-carboxylic acid, mp 268°–72° (diastereomeric mixture). A solution of 7.3 g (0.0263 mole) of the above compound in 10 ml of THF is treated with diborane generated from 7.5 g of NaBH$_4$ in 150 ml of diglyme and 50.6 ml of BF$_3$-etherate in 150 ml of diglyme. After completion of the reaction 30 ml of 6N HCl are added slowly at first. 100 ml of water are added and the THF removed in vacuo. The water solution is adjusted to pH 8-9 with 6N NaOH and extracted with methylenechloride. The gummy residue (6.3 g) is crystallized from ether: 4.2 g (62%) of title compound mp 138°–44° (very likely diastereomeric mixture).

EXAMPLE 5

Preparation of 2,3-Diphenyl-3-Hydroxymethyl-1-Methyl-Pyrrolidine

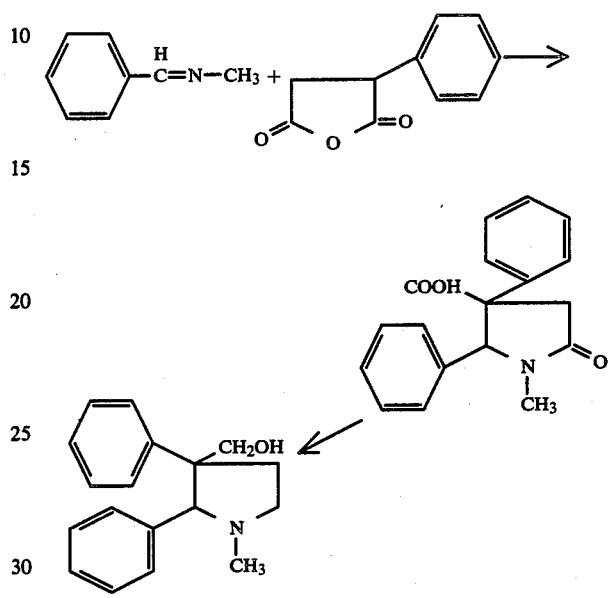

57.5 g (0.327 mole) of phenylsuccinic anhydride and 39 g (0.327 mole) of Schiff base, prepared from benzyldehyde and methylamine according to the general procedure, are refluxed at 140° in 400 ml of xylene for 12 hr. After cooling to 0 C. the solid is collected and washed with xylene and ether: 83.2 g (86% yield) of 2,3-diphenyl-1-methyl-pyrrolidin-5-one-3 carboxylic acid mp 247°–52° (diastereomeric mixture), less polar minor isomer mp 290°–3°, more polar major isomer mp 295°–61° C. 14.7 g of the above acid (0.03 mole) are dissolved in 300 ml of THF and treated at 5°–10° with diborane, generated from 15 g of NaBH$_4$ in 350 ml of diglyme and 101 ml of BF$_3$-etherate in 200 ml of diglyme. After completion of the reaction 250 ml of 6N HCl are added at first very slowly. After the addition of 300 ml of water the THF is removed in vacuo. The water solution is adjusted to pH 8–9 with 6N NaOH. After cooling to 0 the crystals are collected and dried: 9.7 g (74%) of title compound, mp 99°–102° (diastereomeric mixture).

EXAMPLE 6

Preparation of 2,3-Diphenyl-3-Hydroxymethyl-1-(2-Phenylethyl)Pyrrolidine Hydrochloride

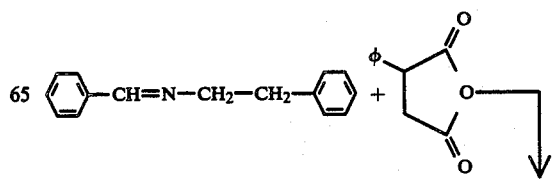

-continued

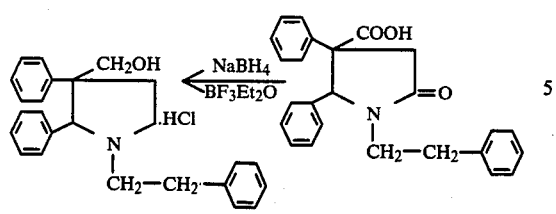

EXAMPLE 7
Preparation of 3-Hydroxymethyl-2-(3-Methoxyphenyl)-3-Phenyl-1-(2-Phenylethyl)-Pyrrolidine Hydrochloride

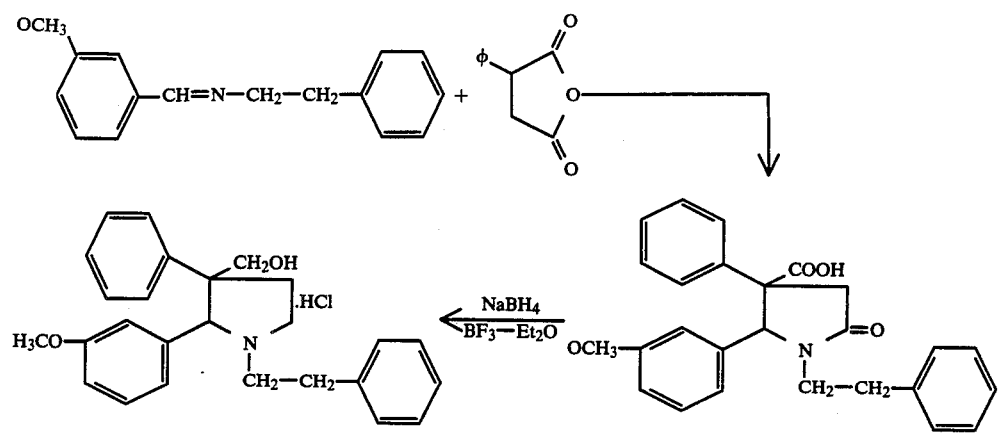

8.8 g (0.05 mole) of phenylsuccinic anhydride and 10.5 g (0.05 mole) of Schiff base, prepared from benzaldehyde and 2-phenylethylamine, are refluxed at 140° in 150 ml of xylene for 5 hr. After cooling the solid is collected and washed with xylene and ether: 11.4 g (59%) of 2,3-diphenyl-1-(2phenylethyl)-pyrrolidin-5-one-3-carboxylic acid mp 207°–9° (one isomer). Concentration of the ML gave additional 3.8 g (20%) of 14b (second isomer contaminated with major isomer, mp 169°–76°. A solution of 10.8 g (0.028 mole) of major isomer in 150 ml of THF is treated with diborane and worked the same as for 32. 10.2 g (100%) of the gummy amine are dissolved in 50 ml of methanol and 2.7 ml of 10N HCl. The solvents are evaporated in vacuo and the residue treated with 100 ml of 2-propanol. After cooling the crystals are collected: 8.7 g (79%) of title compound mp 171°–3°.

8.9 g (0.05 mole) of phenylsuccinic anhydride and 12.7 g (0.05 mole) of Schiff base, prepared from 3-methoxybenzaldehyde and 2-phenylethylamine, are refluxed at 140° in 150 ml of xylene for 5 hr. After cooling the crystals are collected: 12.5 g (60%) of 2-(3-methoxyphenyl)-3-phenyl-1-(2-phenylethyl)pyrrolidine-5-one-3-carboxylic acid isomer) mp 182–4. Concentration of the ML gave additional 4.2 g (20%) of acid (contaminated with major isomer, mp 71°–8°. A solution of 12.5 g (0.03 mole) of major acid in 150 ml of THF is treated with diborane and worked up same as for example 4 11.5 g (99%) of gummyamine are dissolved in 50 ml of methanol and 3.5 ml 10N HCl. Evaporation and crystallization from 120 ml of 2-propanol gave 9.6 g (76%) of title compound, mp 143°–5°.

EXAMPLE 8
Preparation of 3-Hydroxymethyl-3-(3-Methoxyphenyl)-2-Phenyl-1-(2-Phenylethyl)-Pyrrolidine Hydrochloride

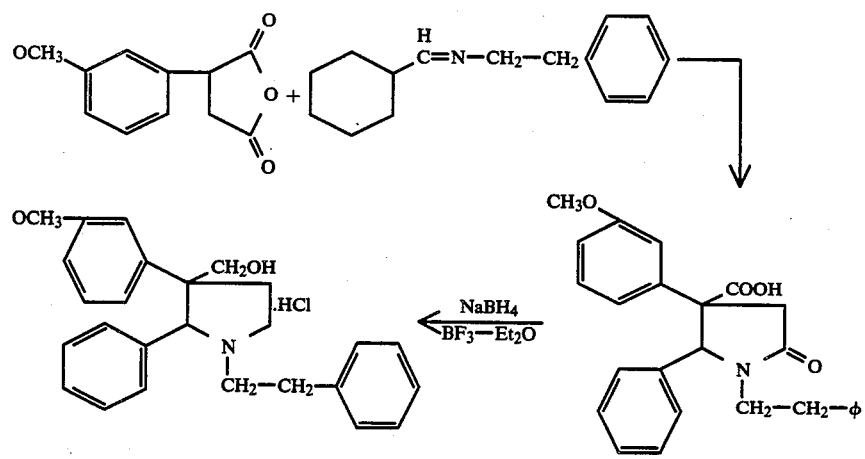

10.3 g (0.05 mole) of (3-methoxyphenyl) succinic anhydride and 10.5 g of Schiff base, prepared from benzaldehyde and 2-phenylethylamine, are refluxed at 140° in 100 ml of xylene for 5 hr. After cooling 10.4 g (50%) of 3-(3-methoxyphenyl)-2-phenyl-1-(2-phenylethyl)-pyrrolidin-5-one-3-carboxylic acid (one isomer) mp 203°-5°, are collected.

A solution of 10.0 g (0.0243 mole) of above acid in 170 ml of THF are treated with diborane and worked up same as for example 4. The 9.2 g (98%) of gummy amine are dissolved in 100 ml of methanol and 3 ml of 10N HCl. Evaporation and crystallization from 2-propanol-acetone-ether/1:2:10 gave 6.8 g (68%) of title compound mp 153°-5° C.

EXAMPLE 9

Preparation of 2-Hydroxymethyl-3-Phenyl-4-(2-Phenylethyl)-Morpholine Hydrochloride

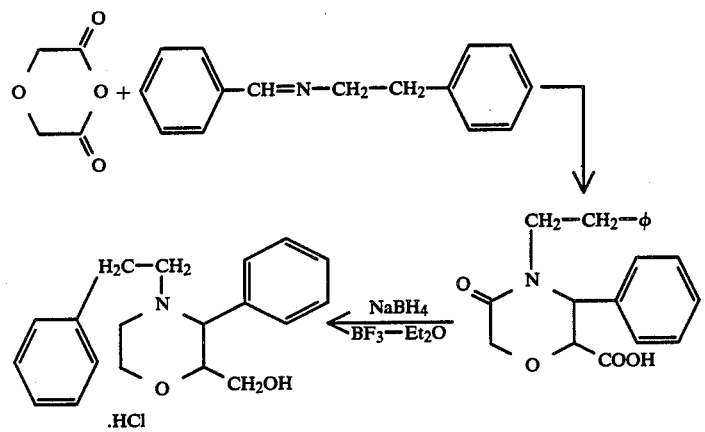

5.2 g (0.05 mole) of diglycolic anhydride and 10.5 g (0.05 mole) of Schiff base, prepared from benzaldehyde and 2-phenylethyamine, are refluxed at 140° in 70 ml of xylene for 5 hr. After cooling the solid is collected: 1.07 g (66%) of 3-phenyl-4-(2-phenylethyl)-morpholin-5-one-2-carboxylic acid mp 138°-44° C.

A solution of 10.5 g (0.032 mole) of the above acid in 150 ml of THF is treated with diborane and worked up same as for example 4. The 9.0 g (95%) of gummy amine are dissolved in 100 ml of methanol and 4 ml of 10N HCl. After evaporation and suspension in ether 10.0 g (94%) of title compound with ¾H₂O, mp 88-94 (probably amorphous), are collected.

EXAMPLE 10

Preparation of 4-Carboxymethyl-5-(2-Methoxy-1-Naphthyl)-N-Phenylpyrrolidin-2-One

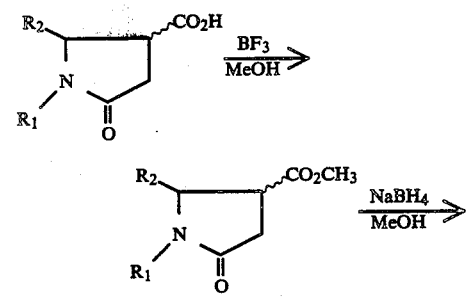

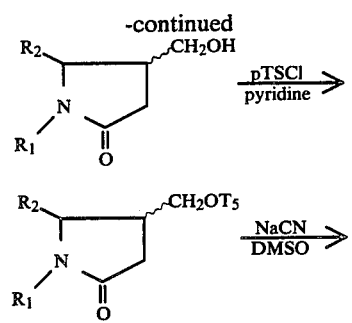

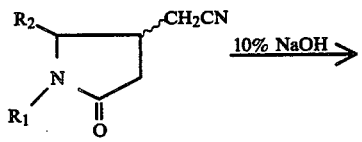

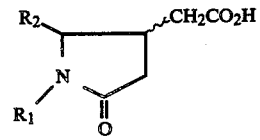

$R_1 = C_6H_5$

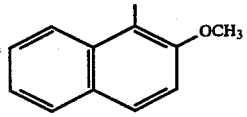

Step I

1-N-phenyl-4-carboxy-5-[2-methoxy-1-naphthyl]pyrrolidin-2-one [32.0 gm 0.089 mole] was treated with methanol [225 ml], boron trifluoride [10.15% in methanol, 75 ml], and refluxed for 3 hours. The solution was cooled to room temperature, the solid filtered and air dried to give a white solid of the methyl ester [29.5 gm 89% yield] having melting point of 168°-169° C.

Step II

The above methyl ester [28.0 gm, 0.075 mole] in methanol [300 ml] was cooled in an ice-bath to 0° C. Sodium borohydride [35.0 gm] was added portion wise with vigorous stirring. The reaction mixture was allowed to stand at room temperature overnight. Then poured into water [1 liter] to give a white emulsion, which was extracted with chloroform, the chloroform dried over sodium sulfate, filtered, and evaporated to dryness to give a white solid [22.6 gm, 87.3% yield.]

Step III

The previous hydroxymethylene compound [21.0 gm, 0.06 mole] was treated with pyridine [200 ml] and cooled in an ice-bath. Para-toluene sulfonyl chloride [25.0 gm 0.13 mole] was added and the reaction mixture kept at 0° C. for 1 hour, then placed in refrigerator overnight. The yellowish liquid was added dropwise, with vigorous stirring, to ice-cold water [1600 ml], the white flocculent precipitate was filtered, washed with ethanol and air dried to give a white solid [27.2 gm, 90% yield].

Step IV

The above tosylate compound [25.0 gm 0.05 mole] was dissolved in dimethylsulfoxide [175 ml]. Sodium cyanide [5.3 gm 0.11 mole] was added and the reaction mixture heated on a steam bath for 5 hours. The reddish solution was added dropwise with vigorous stirring to ice-cold water [1500 ml]. The flocculent precipitate was filtered, washed with ethanol and air dried to give the cyano compound as a beige solid [14.7 gm., 83% yield].

Step V

The above cyano compound [7.0 gm, 0.02 mole] was refluxed with 10% aqueous sodium hydroxide [250 ml] for 5 hours. The clear solution was cooled to room temperature, diluted with water [100 ml] and extracted with chloroform. The aqueous layer was acidified with concentrated hydrochloric acid to give a being solid which was filtered, washed with water and air dried to give the title compound [7.8 gm]. This was recrystallized from ethanol to give a white solid as a mixture of the cis- and trans-4-carboxymethyl-5-(2-methoxy-1-naphthyl)-N-phenyl-pyrrolidin-2-one having a melting point of 198°-203° C.

Analysis: Calculated for $C_{23}H_{21}NO_4$ C, 73.60, H, 5.60, N, 3.70. Found: C, 73.80, H, 5.60, N, 3.59.

EXAMPLE 11

Preparation of 1-N-Phenyl-4-Carboxy-5-[4-Biphenyl]-Pyrrolidin-2-One

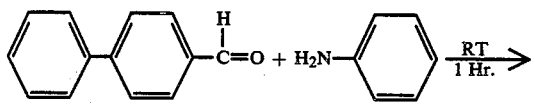

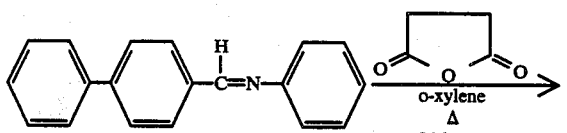

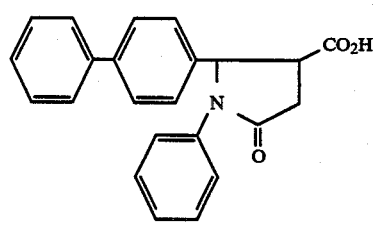

Example 12

Preparation of 1-N-Benzyl-4-Carboxy-5-Phenyl-Pyrrolidin-2-One

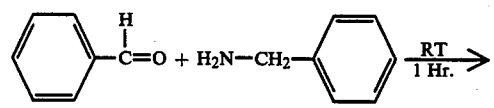

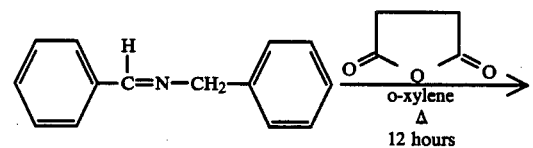

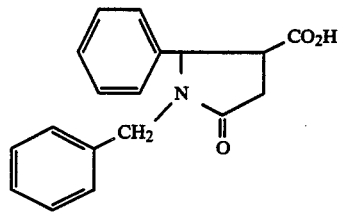

Step I

4-Biphenylcarboxaldehyde [45.5 gm., 0.25 mole] and aniline [23.3 gm., 0.25 mole] were stirred rapidly for one hour at room temperature. The solid reaction mixture was treated with ether [50 ml], filtered and the solid air dried. The white solid was dissolved in chloroform [800 ml], decolorized with charcoal, dried over sodium sulfate, filtered and the chloroform evaporated to dryness to give a white crystalline solid. The white solid of (4-phenyl-benzylidene)-phenylamine, [61.0 gm., 95% yield] after drying under vacuum, had a melting point of 154°-155° C.

Step II (4-phenyl-benzylidene)-phenylamine [60.0 gm., 0.234 mole] and succinic anhydride [23.4 gm., 0.234 mole] were refluxed with o-xylene [150 ml] for 24 hours. On cooling, the precipitated solid was filtered, washed with acetone and air dried. The crude solid [53.5 gm., 64% yield], could be recrystallized from ethyl acetate to give white needless of the title compound having melting point 218°-221° C.

Analysis: Calculated for $C_{23}H_{19}NO_3$ C, 77.31%; H, 5.32%; N, 3.92%. Found: C, 77.30%; H, 5.25%; N, 4.14%.

Step I

Benzaldehyde [212 gm., 2 mole] and benzylamine [214 gm., 2.0 mole] were stirred rapidly at room temperature for one hour. Ether [400 ml] was added to breakup the yellow emulsion. The ether extracts were dried over sodium sulfate, filtered, and evaporated to dryness to give a yellow oil. The oil was distilled under vacuum [0.6 mm.–1.5 mm.] at 115°–135° C. to give a slightly yellow oil [3.60 gm., 93% yield].

Step II

Benzylidene-benzylamine [145.5 gm., 0.75 mole] and succinic anhydride [74.5 gm., 0.745 mole] were refluxed with o-xylene [750 ml.] for 12 hours. The solid, formed upon cooling to room temperature, was filtered, washed with ethanol and air dried. The solid was recrystallized from ethanol to give white needles of the title compound [76.0 gm., 34% yield]. After drying under vacuum and over boiling xylene the solid had a melting point of 169°–171° C.

Analysis: Calculated for $C_{18}H_{17}NO_3$ C, 73.22%; H, 5.76%; N, 4.74%. Found: C, 72.98; H, 5.88%; N, 4.53%.

EXAMPLE 13

Preparation of 1-N-Benzyl-4-Carboxy-5-[2,6-Dichlorophenyl]Pyrrolidin-2-One

Step I 2.6-Dichlorobenzaldehyde [87.5 gm., 0.5 mole] and benzylamine [53.0 gm. 0.5 mole] were strongly agitated with ether for one hour at room temperature. The reaction mixture was dried over sodium sulfate and the etherial solution evaporated to dryness to give a yellow oil. The oil was distilled under vacuum [0.6–1.0 mm.] at a temperature of 145°–165° C. to give a clear oil [104.6 gm. 85% yield]

Step II 2,6-Dichlorobenzylidene-benzylamine [100 gm. 0.39 mole] and succinic anhydride [39.0 gm. 0.39 mole] were refluxed with O-xylene [500 ml] for 12 hours. On cooling, the precipitate was filtered and washed with a little ethanol. The solid was recrystallized from ethanol to give white needles. After drying over boiling isobutyl methyl ketone and under vacuum for 5 hours, the title compound had a melting point of 179°–181° C.

Analysis: Calculated for $C_{18}H_{15}NO_3Cl_2$ C, 59.34; H, 4.13; Cl, 19.51; N, 3.85. Found: C, 60.23; H, 4.35; Cl, 19.47; N, 3.77.

EXAMPLE 14

Preparation of 1-N-Phenyl-4-Carboxy-5[2-Methoxynaphthalene]-Pyrrolidin-2-One

Step I

2-Methoxy-1-naphthaldehyde [50.0 gm. 0.27 mole] and phenylamine [25 gm., 0.27 mole] were refluxed with benzene [100 ml] for 4 hours. The benzene was evaporated to an oil, dissolved in chloroform, the chloroform dried over sodium sulfate and evaporated to a green semisolid of the 2-methoxy-1-naphthylidene-phenylamine [68.8 gm., 97% yield].

Step II

2-Methoxy-1-naphthylidene-phenylamine [30.6 gm., 0.117 mole] and succinic anhydride [11.7 gm., 0.117 mole] were refluxed with xylene [150 ml] for 24 hours. On cooling the yellow solid was filtered, washed with ethanol and recrystallized from acetone to give a mixture of the cis and trans forms of the title compound, having a melting point of 190°–197° C.

Analysis: Calculated for $C_{22}H_{19}NO_4$ C, 73.13%; H, 5.26%; N, 3.88%. Found: C, 72.84; H, 5.45%; N, 3.71%.

EXAMPLE 15

Preparation of 1-Benzyl-6-Phenyl-Piperidin-2-One-5-Carboxylic Acid

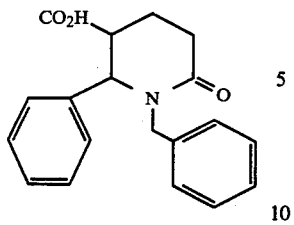

11.4 g (0.10 mole) of glutaric anhydride and 19.5 g (0.10 mole of Schiff base, prepared from benzaldehyde and benzylamine, are refluxed in 300 ml of xylene at 140° C. for 10 hr. After cooling to 0° C. the solid is collected, washed with xylene and ether: 24.7 g (80%) of acid. Recrystallization from acetone-ether gave 21.3 g (69%) of title compound mp 171°-4° C.

EXAMPLE 16

Preparation of 4-(4-Chlorophenyl)-1-Ethyl-5-(3-Methoxyphenyl)Pyrrolidine-2-One-4-Carboxylic Acid

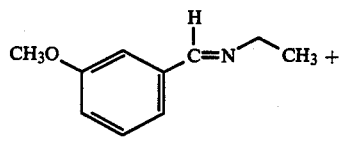

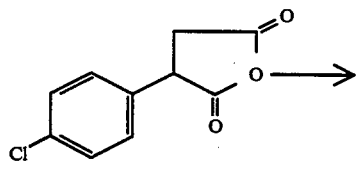

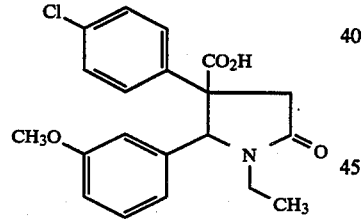

8.13 g of (4-chlorophenyl)-succinic anhydride (0.0386 mole) and 6.3 g (0.0386 mole) of Schiff base, prepared from 3-methoxybenzaldehyde and ethylamine, are refluxed in 100 ml of xylene at 140° C. for 12 hr. After cooling to 0° C. the solid is collected and washed with xylene and ether: 11.5 g (84%) of title compound mp 153°-6° C. (diastereoisomeric mixture).

EXAMPLE 17

Preparation of 1-Benzyl-4-(4-Chlorophenyl)-5-(3-Methoxyphenyl)Pyrrolidin-2-One-4-Carboxylic Acid

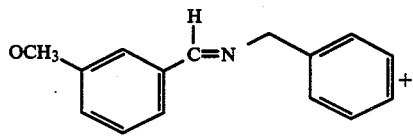

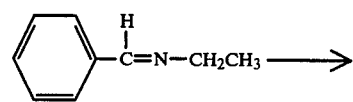

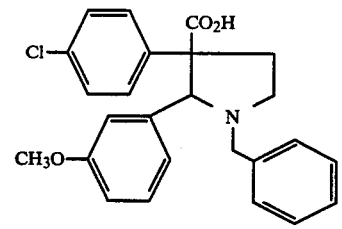

6.3 g (0.03 mole) of (4-chlorophenyl)-succinic anhydride and 6.75 g (0.03 mole) of Schiff base, prepared from 3-methoxybenzaldehyde and benzylamine, according to the general procedure, are refluxed at 140° C. in 90 ml of xylene for 12 hr. After cooling to 0° C. the solid is collected, washed with xylene and ether: 9.15 g (70%) of title compound mp 76°-8° C.

EXAMPLE 18

Preparation of 4-Benzyl-3-Phenyl-Morpholin-5-One-2-Carboxylic Acid

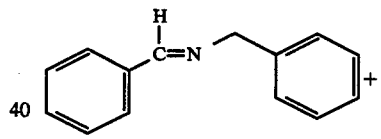

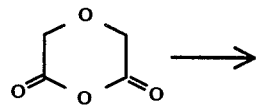

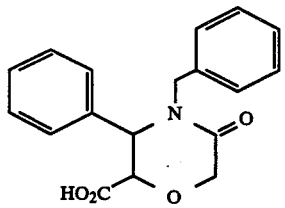

9.86 g (0.085 mole) of diglycolic anhydride and 16.5 g of Schiff base (0.085 mole), prepared from benzyldehyde and benzylamine, are refluxed at 140° C. in 220 ml of xylene for 6 hr. After cooling to 0° C. the solid is collected and washed with ether: 14.5 g (54%) mp 170°-9° C. Recrystallization from methylenechloride (little) and ether gave 11.3 g (43%) of title compound mp 177°-81° C.

EXAMPLE 19

Preparation of 4-Benzyl-3-Phenyl-1,4-Perhydrothiazin-5-One-2-Carboxylic Acid

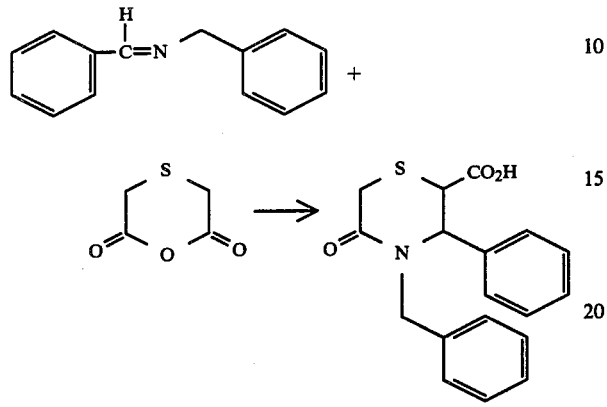

9.1 g (0.07 mole) of thiodiglycolic anhydride and 13.2 g (0.07 mole) of Schiff base, prepared from benzaldehyde and benzylamine, are refluxed at 140° in 120 ml of xylene for 6 hr. After cooling to 0° the solid is collected and washed with ether: 7.3 g (32%) of title compound mp 132°–4° C.

EXAMPLE 20

1-Methyl-2-Phenyl-5-Oxopyrrolidin-3-Acetic Acid

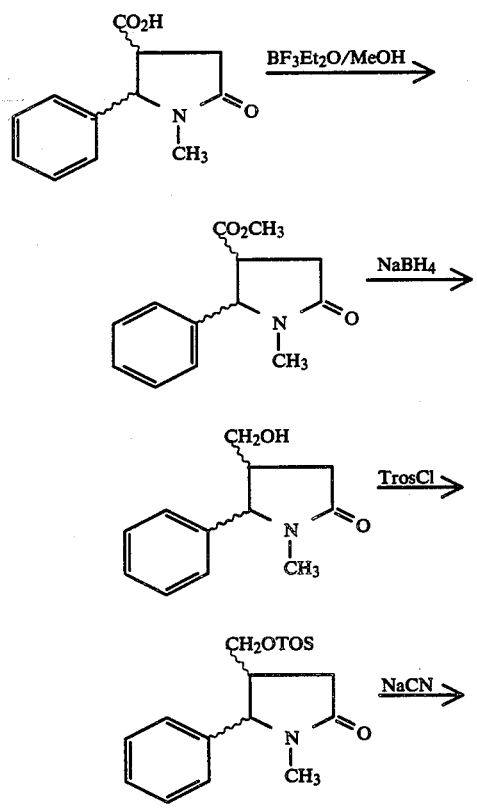

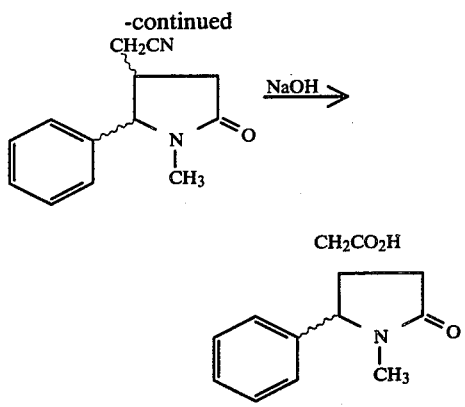

(A) Methyl 1-Methyl-5-oxo-2-phenylpyrrolidin-3-carboxylate

To 400 ml. of methanol containing 25 ml. of boron trifluoride etherate was added 60 g of 1-methyl-5-oxo-2-phenylpyrrolidin-3-carboxylic acid and the solution refluxed for 8 hours. Concentration in vacuo provided an oil which was dissolved in chloroform. The chloroform solution was washed with a saturated sodium carbonate solution, a saturated sodium bicarbonate solution, water, a saturated sodium chloride solution and dried ($Na_2SO_4$). Titration and concentraion in vacuo provided 63 g. of an oil.

(B) 3-Hydroxymethyl-1-methyl-2-phenylpyrrolidin-5-one

To 82.6 g. of sodium borohydride in 950 ml. of methanol at −5° to 0° C. was slowly added in portions 63 g. of methyl 1-methyl-5-oxo-2-phenylpyrrolidin-3-carboxylate. After the addition, the reaction mixture was then allowed to come to ambient temperature over 2 hours. Concentration in vacuo gave a semisolid which was suspended in water at 50° C. and stirred for 30 minutes. The solid was then dissolved in 3:1 chloroform-ether, dried ($Na_2SO_4$) filtered, and concentrated in vacuo to yield 40 g. of an oil.

(C) 1-Methyl-2-phenyl-3-tosyloxymethyl-pyrrolidin-5-one

To 27.8 g. of 3-hydroxymethyl-1-methyl-2-phenyl-pyrrolidin-5-one in 40 ml. of potassium hydroxide dried pyridine was added in portions of 0°–5° 29.4 g. of p-toluenesulfonyl chloride. The orange solution was then stirred at 15° C. for 4 hours and then decanted into 180 ml. of ice cold 10% hydrochloric acid. The resulting solid was collected by filtration and washed with water and air dried. Washing with ether provided 37 g. of crude product.

(D) 3-Cyanomethyl-1-methyl-2-phenyl-pyrrolidin-5-one

To 42 g. of 1-methyl-2-phenyl-3-tosyloxymethyl-pyrrolidin-5-one in 72.5 ml. of dimethylsulfoxide was slowly added 5.7 g of sodium cyanide at 45° C. The reaction was stirred for 3 hours at 100° C. and then set at ambient temperature for 18 hours. After decanting into 1500 ml. of ice water, the product was extracted with 2:1 chloroform-ether, dried ($Na_2SO_4$) filtered, and concentrated in vacuo to provide 19.0 g. of light yellow crystals.

(E) 1-Methyl-2-phenyl-5-oxopyrrolidin-3-acetic acid

A Mixture of 19.0 g. of 3-cyanomethyl-1-methyl-2-phenyl-pyrrolidin-5-one, 64.0 g. of sodium hydroxide, and 567 ml. of water was refluxed for 8 hours and then set for 16 hours at ambient temperature. The solution was diluted with 300 ml. of water and filtered to remove some insoluble material. Acidification of the ice cooled aqueous phase with concentrated hydrochloric acid provided a solid. The solid was collected by filtration, washed with water, and dissolved in chloroform. Drying ($Na_2SO_4$), filtration, and concentration in vacuo gave a yellow solid which upon recrystallization from acetonitrile provided 12.0 g. of off-white crystals, mp 166°–170°.

Analysis: Calculated for $C_{13}H_{15}NO_3$: %C, 66.93; %H, 6.48; %N, 6.01. Found: %C, 66.70; %H, 6.70; %N, 5.92.

EXAMPLE 21

Preparation of 1-Benzyl-2-(2,3-Dichlorophenyl)-5-Oxo-Pyrrolidin-3-Acetic Acid

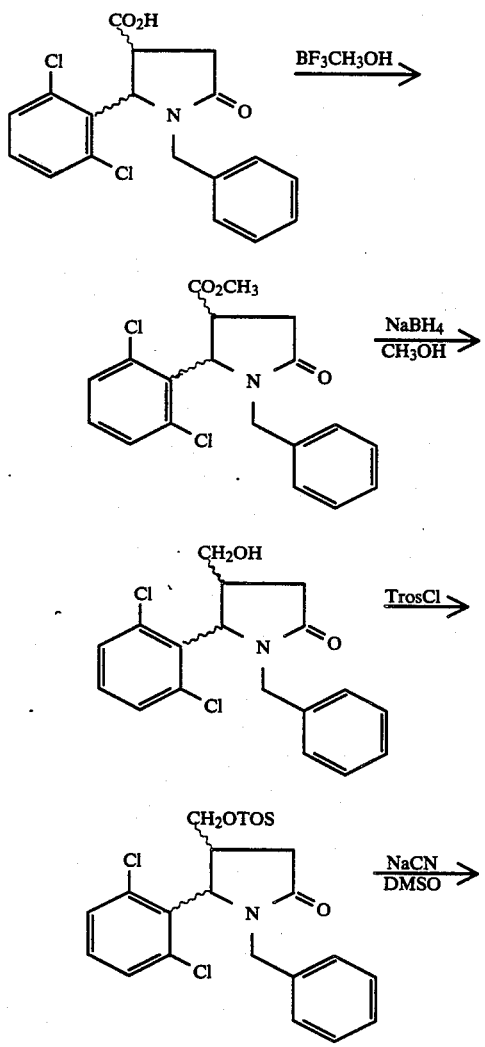

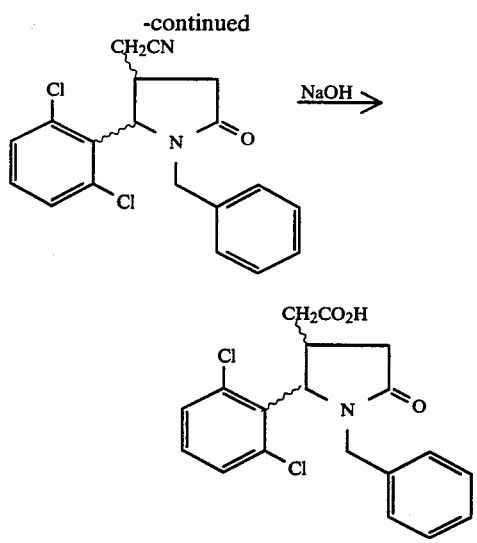

(A) Methyl 1-Benzyl-2-(2,6-dichlorophenyl)-5-oxopyrrolidin-3-carboxylate

A solution of 25 g of 1-benzyl-2-(2,6-dichlorophenyl)-5-oxopyrrolidin-3-carboxylic acid in 247 ml of boron trifluoride methanol was refluxed for 7 hours and then concentrated in vacuo to a solid. The solid was dissolved in chloroform and the chloroform washed with a saturated sodium carbonate solution and then with a saturated sodium bicarbonate solution. Drying ($Na_2SO_4$), filtration, and concentration in vacuo provided 18 g of off-white crystals, m.p. 97°–102°.

(B) 1-Benzyl-2-(2,6-dichlorophenyl)-3-hydroxymethyl-pyrolidin-5-one

To 580 ml of methanol was added 72 g. of sodium borohydride at 0°–5°. After the addition, 40 g of methyl 1-benzyl-2-(2,6-dichlorophenyl)-5-oxopyrrolidin-3-carboxylate was then added in portions at 0°–5°. The reaction was stirred at 10°–15° and then left standing overnight at ambient temperature. After concentrating the mixture in vacuo to a solid, the crude product was suspended in water at 50° and stirred for 30 minutes. The resulting solid was collected by filtration and dissolved in chloroform. Drying ($Na_2SO_4$), filtration, and concentration in vacuo provided 48 g of off-white crystals, m.p. 122°–126°.

(C) 1-Benzyl-2-(2,6-dichlorophenyl)-3-tosyloxymethyl-pyrolidin-5-one

To 40 g of 1-benzyl-2-(2,6-dichlorophenyl)-3-hydroxymethyl-pyrrolidine-5-one in 67 ml of potassium dried pyridine at 5°–10° was added 23.3 g of tosyl chloride over 30 minutes. After the addition, the mixture was stirred for 3 hours at 15° and then for 13 hours at ambient temperature. The reaction mixture was added dropwise to a stirred ice-water solution and then set at ambient temperature for 72 hours. The light yellow solid was collected by filtration and then air dried. Trituration with ether followed by filtration provided 44.5 g of colorless crystals, m.p. 110°–114°.

(D) 1-Benzyl-2-(2,6-dichlorophenyl)-3-cyanomethyl-pyrrolidin-5-one

To 40 g. of 1-benzyl-2-(2,6-dichlorophenyl)-3-tosyloxymethyl-pyrrolidin-5-one in 50 ml of dimethylsulfoxide was slowly added 3.92 g sodium cyanide at 45°. The reaction was then stirred for 48 hours at ambient temperature and then at 100° C. for 2 hours. The cooled reaction mixture was slowly added to 1500 ml of ice water with stirring to yield a gummy material which upon further stirring and setting overnight at ambient temperature provided 25 g of crude product after vacuum drying for 18 hours.

(E) 1-Benzyl-2-(2,6-dichlorophenyl)-pyrrolidin-3-acetic acid

To 90 ml of water containing 10 g of sodium hydroxide was added 5.0 g of 1-benzyl-3-cyanomethyl-2-(2,6-dichlorophenyl)-pyrrolidin-5-one. The reaction was refluxed 5 hours, cooled, and filtered. Extraction of the aqueous phase with ether followed by addition of ice and acidification with concentrated hydrochloric acid gave a solid which was then triturated with ether to yield beige crystals. Vacuum drying (0.1 Torr) under refluxing toluene for 15 hours followed by recrystallization from ethanol provided upon drying 1.50 g of colorless crystals, m.p. 186°–188°.

Analysis: Calculated for $C_{19}H_{17}Cl_2NO_3$ %C, 60.33; %H, 4.53; %N, 3.70; %Cl, 18.75. Found: %C, 59.90; %H, 4.40; %N, 3.53; %Cl, 18.71.

EXAMPLE 22

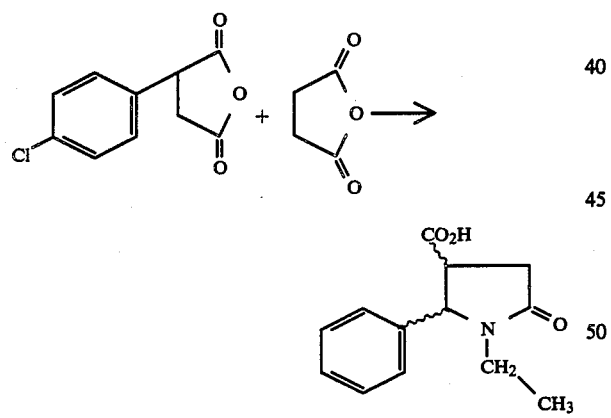

Preparation of 1-Ethyl-5-Oxo-2-Phenyl-Pyrrolidin-3-Carboxylic Acid

A mixture of 42 g of Schiff base (prepared from 42.4 g of benzaldehyde and 23.5 g of 70% aqueous ethylamine), 32 g of succinic anhydride, and 200 ml of xylene was refluxed for 24 hours. The reaction was cooled and the precipitate collected by filtration. The crude product was then recrystallized once from ethyl acetate and then from ethanol to yield the product as the first crop of crystals, 5.3 g, m.p. 151°–156°.

Analysis: Calculated for $C_{13}H_{15}NO_3$ %C, 66.93; %H, 6.48; %N, 6.01. Found: %C, 66.95; %H, 6.31; %N, 6.18.

EXAMPLE ≦

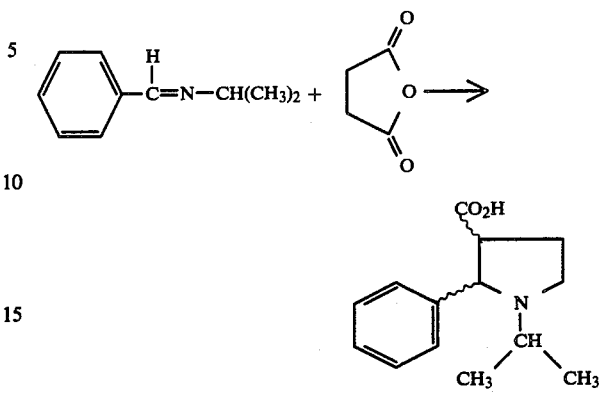

Preparation of 1-Isopropyl-2-Phenyl-5-Oxopyrrolidin-3-Carboxylic Acid

A mixture of 29.4 g of Schiff base (prepared from 21.2 g of benzaldehyde and 12.0 g of isopropylamine), 20 g of succinic anhydride, and 50 ml of xylene was refluxed for 24 hours. The reaction was diluted with ether and extracted with a saturated sodium bicarbonate solution. Ice as added to the basic phase followed by acidification with concentrated hydrochloric acid. The precipitate was dried and then recrystallized from ethyl acetate to provide 6.0 g of colorless crystals, m.p. 126°–134°.

Analysis: Calculated for $C_{14}H_{17}NO_3$ %C, 67.99; %H, 6.93; %N, 5.67. Found: %C, 67.93; %H, 7.08 %N, 5.54.

EXAMPLE 24

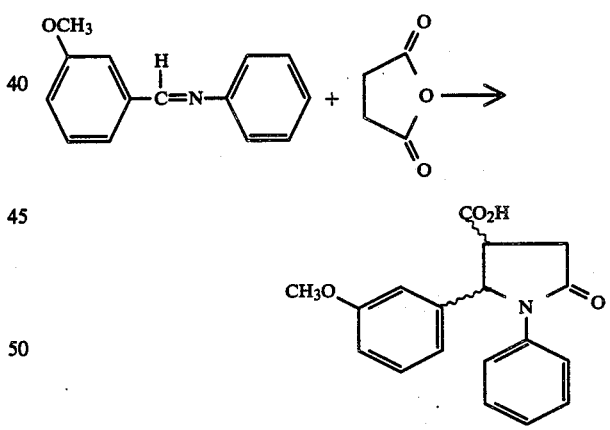

Preparation of 1-Phenyl-2-(3-Methoxyphenyl)-5-Oxopyrrolidin-3-Carboxylic

A mixture of 42.3 g of Schiff base (prepared from 85.4 g of 3-methoxybenzaldehyde and 58.7 g of aniline), 20.0 g of succinic anhydride, and 200 ml of xylene was refluxed for 16 hours. The reaction was then cooled and extracted with a saturated sodium bicarbonate solution. Ice as added to the basic solution followed by acidification with concentrated hydrochloric acid. The gummy precipitate was collected by filtration; treatment with ether gave a solid. Recrystallization from ethyl acetate followed by a second recrystallization from acetonitrile provided 21.0 g of off-white crystals, m.p. 145°–149°.

Analysis: Calculated for $C_{18}H_{17}NO_4$ %C, 69.44; %H, 5.51; %N, 4.50. Found: %C, 69.11; %H, 5.41; %N, 4.35.

EXAMPLE 25

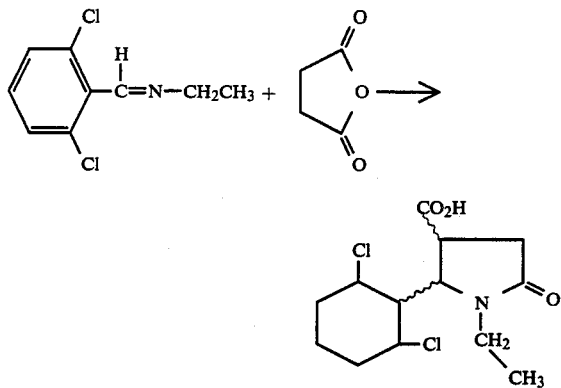

Preparation of 2-(2,6-Dichlorophenyl)-1-Ethyl-5-Oxopyrrolidin-3-Carboxylic Acid

A mixture of 65.0 g of Schiff base (prepared from 70 g of 2,6-dichlorobenzaldehyde and 23.5 g of 70% aqueous ethylamine), 32.2 g of succinic anhydride, and 200 ml of xylene was refluxed for 24 hours. The reaction was cooled, diluted with ether, and extracted with a saturated sodium bicarbonate solution. Ice was added to the basic phase which upon acidification with concentrated hydrochloric acid provided a solid. Recrystallization from ethyl acetate gave 6.9 g of colorless crystals, m.p. 195°–197°.

Analysis: Calculated for $C_{13}H_{13}Cl_2NO_3$ %C, 51.67; %H, 4.34; %Cl, 23.47; %N, 4.64.

Found: %C, 51.67; %H, 4.44; %Cl, 23,60; %N, 4.59.

In all of the above examples, the temperature degrees are in centigrade.

While the invention has been illustrated in particular with respect to specific compounds of the above general formula, it is apparent that variations and modifications of the invention can be made.

What is claimed is:

1. The compound 1-benzyl-4-N,N-dimethylaminomethyl-5-(3-methoxyphenyl)-pyrrolidin-2-one.

2. The compound 4-dimethylaminomethyl-5-(3-methoxyphenyl)-1-phenyl pyrrolidin-2-one.

3. The compound 1-benzyl-4-N,N-dimethylaminomethyl-5-(3-hydroxyphenyl)-pyrrolidin-2-one.

* * * * *